United States Patent
Wooley et al.

(10) Patent No.: US 6,851,803 B2
(45) Date of Patent: Feb. 8, 2005

(54) OPHTHALMIC LENSES WITH REDUCED CHROMATIC BLUR

(76) Inventors: C. Benjamin Wooley, 5115 Elk Hill Dr., Roanoke, VA (US) 24014; Amitava Gupta, 5322 Fox Den Rd., Roanoke, VA (US) 24014; Israel Grossinger, 19 Yakob St., Rehovot (IL), 76262

( * ) Notice: Subject to any disclaimer, the term of this patent is extended or adjusted under 35 U.S.C. 154(b) by 0 days.

(21) Appl. No.: 10/279,619

(22) Filed: Oct. 24, 2002

(65) Prior Publication Data

US 2004/0080710 A1 Apr. 29, 2004

(51) Int. Cl.⁷ ............................................. G02C 7/02
(52) U.S. Cl. .................. 351/159; 351/161; 351/168; 351/177
(58) Field of Search .................. 351/160 R, 160 H, 351/161, 162, 159, 41, 168, 170–172, 177; 623/6.3, 6.31, 6.24–6.27

(56) References Cited

U.S. PATENT DOCUMENTS

| | | | |
|---|---|---|---|
| 4,637,697 A | 1/1987 | Freeman | 351/161 |
| 4,641,934 A | 2/1987 | Freeman | 351/159 |
| 4,642,112 A | 2/1987 | Freeman | 623/6.3 |
| 4,655,565 A | 4/1987 | Freeman | 351/159 |
| 4,830,481 A | 5/1989 | Futhey et al. | 351/161 |
| 4,881,805 A | 11/1989 | Cohen | 351/161 |
| 5,013,133 A | 5/1991 | Buralli et al. | 359/558 |
| 5,016,226 A | 5/1991 | Freeman | |
| 5,016,977 A | 5/1991 | Baude et al. | 359/570 |
| 5,076,684 A | 12/1991 | Simpson et al. | 351/168 |
| 5,078,513 A | 1/1992 | Spaulding et al. | 385/14 |
| 5,089,023 A | 2/1992 | Swanson | 623/6.25 |
| 5,096,285 A * | 3/1992 | Silberman | 351/161 |
| 5,104,212 A | 4/1992 | Taboury et al. | |
| 5,114,220 A | 5/1992 | Baude et al. | |
| 5,116,111 A | 5/1992 | Simpson et al. | |
| 5,129,718 A | 7/1992 | Futhey et al. | |
| 5,152,788 A | 10/1992 | Isaacson et al. | |
| 5,281,294 A | 1/1994 | Freeman et al. | |
| 5,331,132 A | 7/1994 | Freeman et al. | |
| 5,344,447 A | 9/1994 | Swanson | 623/6.3 |
| 5,349,394 A * | 9/1994 | Freeman et al. | 351/160 R |
| 5,349,471 A | 9/1994 | Morris et al. | |
| 5,371,570 A | 12/1994 | Morris et al. | |
| 5,384,606 A | 1/1995 | Koch et al. | 351/158 |
| 5,699,142 A | 12/1997 | Lee et al. | |
| 5,715,091 A | 2/1998 | Meyers | 359/365 |
| 5,734,502 A | 3/1998 | Ebstein | 359/569 |
| 5,895,422 A * | 4/1999 | Hauber | 623/6.31 |
| 5,978,159 A | 11/1999 | Kamo | 359/793 |
| 6,070,980 A | 6/2000 | Obara et al. | 351/159 |
| 6,139,147 A * | 10/2000 | Zhang | 351/161 |

OTHER PUBLICATIONS

Hecht, Eugene; Optics; 1987; Second Edition; pp. 181–184.*
PCT International Search Report, dated Mar. 24, 2004, for PCT Int'l. Appln. No. PCT/US03/33180.

* cited by examiner

Primary Examiner—Jordan M. Schwartz
(74) Attorney, Agent, or Firm—Lois Gianneschi

(57) ABSTRACT

The present invention provides single vision and multifocal lenses, as well as methods for their production, having a transverse chromatic aberration enabling provision of a lens the performance of which is equivalent to a refractive lens with a higher Abbe number.

16 Claims, 8 Drawing Sheets

OPHTHALMIC LENSES WITH REDUCED CHROMATIC BLUR

FIELD OF THE INVENTION

The present invention relates to ophthalmic lenses. In particular, the invention is directed to spectacle lenses in which chromatic aberration is reduced.

BACKGROUND OF THE INVENTION

The use of ophthalmic lenses for the correction of ametropia is well known. In the manufacture of spectacle lenses, it is desirable to use high refractive index materials, or materials with a refractive index greater than 1.50, in order to provide acceptable edge and center thicknesses, especially in higher power lenses. However, increasing the refractive index using conventional materials such as polycarbonate or inorganic glass results in an increase in chromatic aberration or color dispersion.

Longitudinal and transverse chromatic aberration is caused by the displacement of images formed by light of different wavelengths. The magnitude of the aberration depends on the power of the lens and the physical properties of the lens material. Persons wearing spectacle lenses made of conventional materials will experience chromatic aberration to varying degrees, especially in the periphery of their visual fields.

For a refractive single element lens, typical for a spectacle lens, the lens' transverse chromatic aberration ("TCA") in diopters depends upon the Abbe number (V), the lens power($\Phi$) in diopters, and the gaze height on the lens from the lens center (y) in millimeters as shown in Equation I.

$$TCA = 0.1 \cdot y \cdot \frac{\Phi}{V} \quad (I)$$

The following table shows the TCA for various lens powers and Abbe values at a gaze height of 15 mm.

TABLE 1

| | Transverse Chromatic Aberration in Diopters | | | | | | | | | |
|---|---|---|---|---|---|---|---|---|---|---|
| | Lens Power in Diopters | | | | | | | | | |
| Abbe Value - V | 1 | 2 | 3 | 4 | 5 | 6 | 7 | 8 | 9 | 10 |
| 25 | 0.06 | 0.12 | 0.18 | 0.24 | 0.30 | 0.36 | 0.42 | 0.48 | 0.54 | 0.60 |
| 30 | 0.05 | 0.10 | 0.15 | 0.20 | 0.25 | 0.30 | 0.35 | 0.40 | 0.45 | 0.50 |
| 35 | 0.04 | 0.09 | 0.13 | 0.17 | 0.21 | 0.26 | 0.30 | 0.34 | 0.39 | 0.43 |
| 40 | 0.04 | 0.08 | 0.11 | 0.15 | 0.19 | 0.23 | 0.26 | 0.30 | 0.34 | 0.38 |
| 45 | 0.03 | 0.07 | 0.10 | 0.13 | 0.17 | 0.20 | 0.23 | 0.27 | 0.30 | 0.33 |
| 50 | 0.03 | 0.06 | 0.09 | 0.12 | 0.15 | 0.18 | 0.21 | 0.24 | 0.27 | 0.30 |
| 55 | 0.03 | 0.05 | 0.08 | 0.11 | 0.14 | 0.16 | 0.19 | 0.22 | 0.25 | 0.27 |
| 60 | 0.03 | 0.05 | 0.08 | 0.10 | 0.13 | 0.15 | 0.18 | 0.20 | 0.23 | 0.25 |

The TCA becomes problematic to many wearers if it is greater than 0.25 diopters.

Typical conventional high refractive index materials have Abbe numbers from 30 to 45, which will cause problems for some wearers. Some low refractive index materials that are considered low dispersion will have Abbe numbers greater than 55, which gives acceptable chromatic performance to the vast majority of wearers. However, high refractive index materials are desirable for spectacle lenses because they permit production of thinner and lighter weight lenses. Therefore, a need exists for a high refractive index material for spectacle lens use that can provide chromatic performance equivalent to low refractive index lenses with large Abbe numbers.

DESCRIPTION OF THE INVENTION AND ITS PREFERRED EMBODIMENTS

Figure 1:
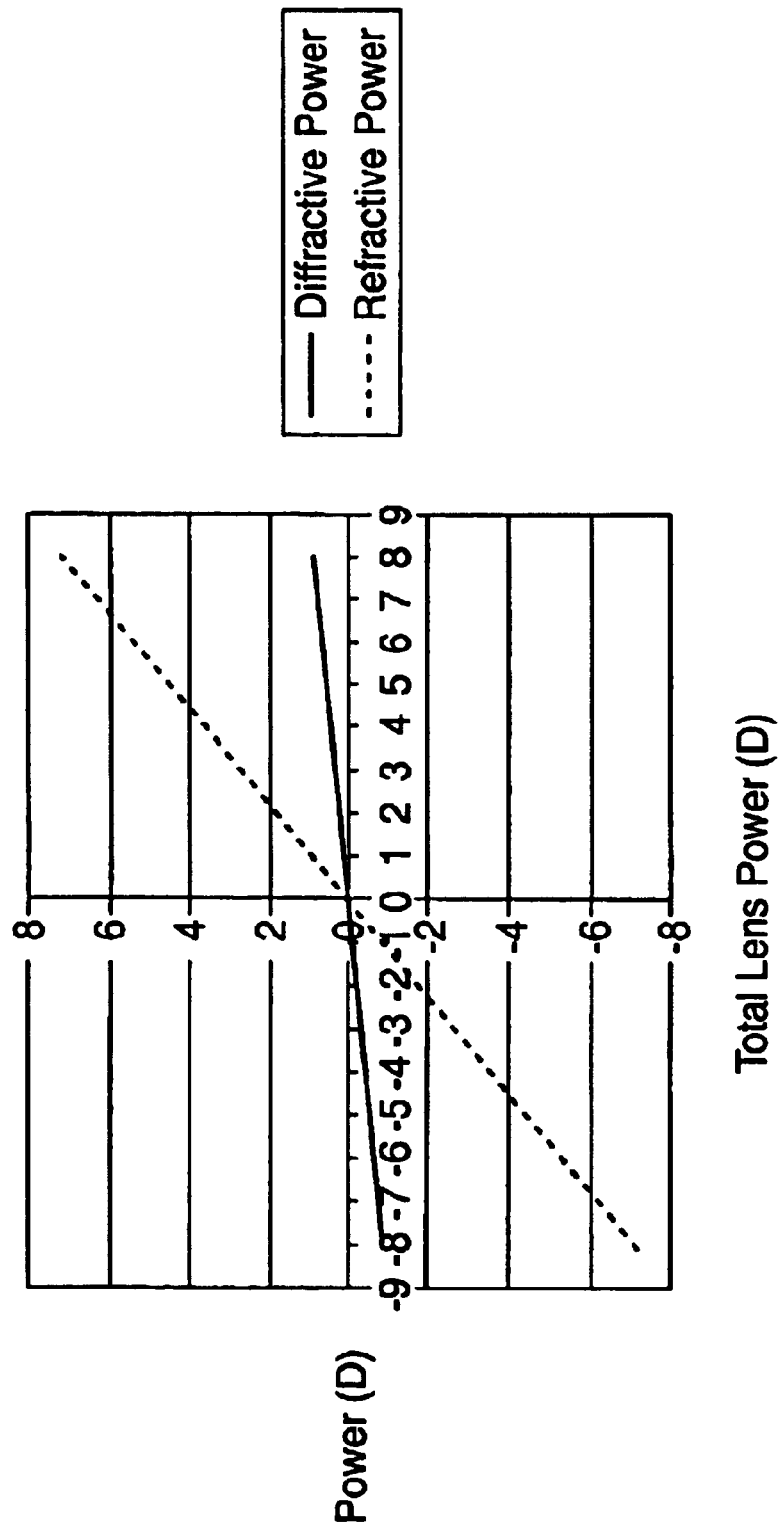
FIG. 1 is a graphical representation of the ideal refractive and diffractive powers for minimum chromatic aberration.

The present invention provides single vision and multifocal lenses, as well as methods for their production, in which both diffractive and refractive elements are used. This composite lens reduces, by about 10 to 100%, transverse chromatic aberration enabling provision of a high refractive index lens that has an effective Abbe number of about 50 to 120. By combining refractive and diffractive powers in a specified balance, a lens may be provided with performance equivalent to a refractive lens with a higher Abbe number.

In one embodiment, the invention provides an ophthalmic lens comprising, consisting essentially of, and consisting of spherical power $\Phi$, a diffractive element comprising a first spherical power $\Phi_D$ and a refractive element comprising a second spherical power $\Phi_R$ wherein $\Phi=\Phi_D+\Phi_R$. By "ophthalmic lens" is meant a lens suitable to correct visual acuity including, without limitation spectacle, contact, intraocular, onlay lenses and the like.

For a single vision lens, $\Phi$ may be the average spherical power throughout the lens, the local spherical power at the optical center, or the local spherocylindrical power at the optical center. One ordinarily skilled in the art will recognize that the value of $\Phi_D$ will depend upon the spherical power selected and the desired level of correction of TCA. For a multifocal lens, $\Phi$ may be the spherical or spherocylindrical power at the optical center or fitting, the power at the center of the near vision region of the lens, or the local power varying throughout the optic in which case $\Phi_D$ will vary throughout the lens.

The diffractive element may be any suitable element including, without limitation, a diffractive grating, a hologram, a kinoform, and the like. The power provided by the diffractive element may be positive or negative power.

The ideal TCA correction may be achieved by requiring that:

$$\left| \frac{\Phi_R}{V_R} + \frac{\Phi_D}{V_D} \right| = 0 \tag{II}$$

wherein $V_R$ is the Abbe number of the lens material and $V_D$ is the effective Abbe number of the diffractive element of the lens. Typically, the lens material Abbe number will be about 30 to about 60.

The Abbe number of the diffractive element may be defined as:

$$V_D = \frac{\lambda_{mid}}{\lambda_{short} - \lambda_{long}} \tag{III}$$

where $\lambda_{mid}$ is the wavelength of the midpoint of the range of interest. For visible systems a value of 587 nm is typically used. The short wavelength of the range of interest is $\lambda_{short}$ and for visible systems a value of 486 nm is typically used. The long wavelength of the range of interest is $\lambda_{long}$. For visible systems 656 nm is typically used. Using these wavelength values, $V_D$ is −3.45.

The diffractive power required for the lens may be obtained by solving Equation IV resulting in:

$$\Phi_D = \frac{\Phi}{1 - \frac{V_R}{V_D}} \tag{IV}$$

Preferably, the diffractive element adds about 0.10 to about 1.50 diopters of spherical power.

The diffractive element may cover substantially the entire, or a portion of, the back, or concave surface, front, or convex surface, or a surface intermediate the front or back surface of the lens. The diffractive element may be of any shape including, without limitation, annular, circular, elliptical, and the like. Preferably, the diffractive element covers the back surface for purposes of ease of manufacture and for cosmetic durability. In the embodiment in which the diffractive element is intermediate to the front and back surfaces, the change in refractive index across the intermediate layer must be such that it enables the diffractive element to function. Typically, the change in refractive index must be between 0 and 0.25 units per micron.

FIG. 1 is a graph depicting the preferred combination of refractive and diffractive spherical power for total lens powers of polycarbonate lenses of from −9.00 to +9.00 diopters assuming that $V_R$ is 30. One of ordinary skill in the art will realize that for materials with a larger $V_R$, less diffractive power will be required. A reduction in chromatic aberration may be realized with diffractive powers meeting the following criteria:

$$2 \left| \frac{\Phi}{1 - \frac{V_R}{V_D}} \right| > |\Phi_D| > 0 \tag{V}$$

In this equation, $\Phi_D$ is defined as the optimum value of the diffractive power for a refractive power $\Phi_R$ and its value may be from about 0 to about $2\Phi_D$. If the value is 0, there is no correction of chromatic aberration. If the value is $2\Phi_D$, then the chromatic aberration if equal to that of the lens but in the opposite direction.

Preferably however, the diffractive power is limited to $$1.9 \left| \frac{\Phi}{1 - \frac{V_R}{V_D}} \right| > |\Phi_D| > 0.1|\Phi_D| \tag{VI}$$

More preferably, the diffractive power is limited to:

$$1.5 \left| \frac{\Phi}{1 - \frac{V_R}{V_D}} \right| > |\Phi_D| > .5|\Phi_D| \tag{VII}$$

Figure 2:
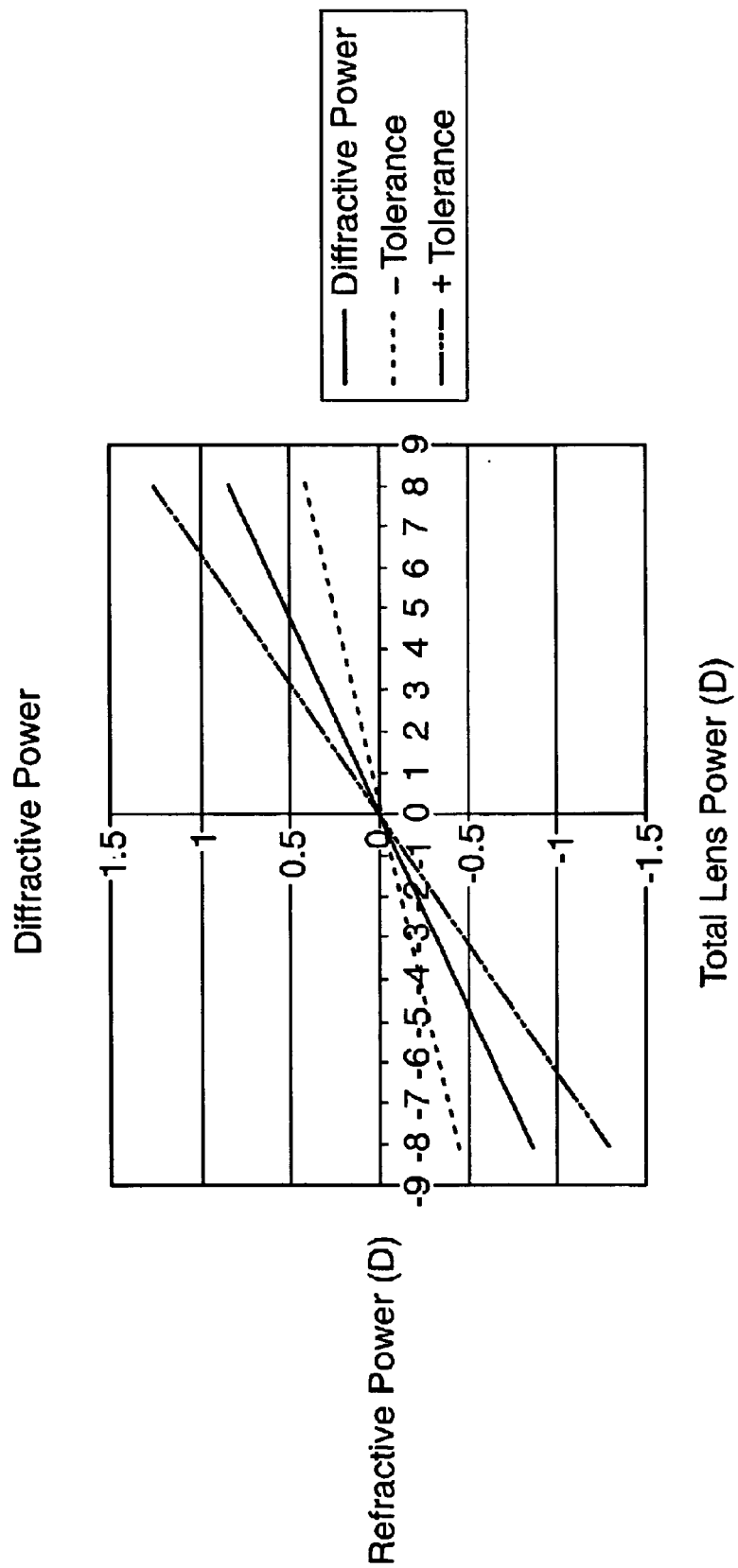
FIG. 2 is a graphical representation of the range of diffractive powers that will give at least a 50% reduction in chromatic aberration for spherical lens powers from −9 to 9 diopters.

FIG. 2 depicts the $\Phi_D$ using Equation II and plotted along the positive and negative tolerance limits as given by the Equation VII. If the diffractive power is within the limits provided by Equation VII, then the transverse chromatic aberration is reduced by at least 50%. Although it may be desirable for optimum TCA correction to require the diffractive power to satisfy Equation II, the relaxed constraint provided by Equation VII allows the chromatic performance to be improved to be equivalent to or better than that provided for with low index, high Abbe number glasses without requiring a unique diffractive element for every spherical power.

Equation V may be cast in an alternate form so that the diffractive power is defined in terms of the maximum allowable TCA. In this form, for low lens spherical powers that inherently have small amounts of transverse chromatic aberration, the solution allows for only refractive power. In this form, the constraint on the diffractive power is:

$$\left[ V_D \cdot \frac{\left( \frac{-TCA}{0.1 \cdot y} \cdot V_R - \Phi \right)}{V_R - V_D} \right] > \Phi_D > V_D \cdot \frac{\left( \frac{TCA}{0.1 \cdot y} \cdot V_R - \Phi \right)}{V_R - V_D} \tag{VIII}$$

The lenses of the invention may be fabricated by any convenient means and constructed of any known material suitable for production of ophthalmic lenses. Suitable materials include, without limitation, polycarbonate, allyl diglycol, polymethacrylate, and the like. Such materials are either commercially available or methods for their production are known. Further, the lenses may be produced by any conventional lens fabrication technique including, without limitation grinding, whole lens casting, molding, thermoforming, laminating, surface casting, or combinations thereof. Casting may be carried out by any means, but preferably is performed by surface casting including, without limitation, as disclosed in U.S. Pat. Nos. 5,147,585, 5,178,800, 5,219,497, 5,316,702, 5,358,672, 5,480,600, 5,512,371, 5,531,940, 5,702,819, and 5,793,465 incorporated herein in their entireties by reference.

The diffractive element may be provided through a molding process using optical tools incorporating the required diffractive elements. Such tools include, without limitation, metal inserts suitable for injection or compression molding of plastic optical parts, glass or metal molds for casting of optical parts, and metal or ceramic stamping tools. Alternatively, the diffractive element may be provided by diamond turning. The finished element may be coated with a suitable coating that conforms to the element and preserves the function of the diffractive element. Alternatively, a non-conforming coating may be used to effectively bury the diffractive element under the coating. In this embodiment, the width and depth of the individual grating elements will have to take into account the difference on refractive index between the coating and the substrate. Suitable coatings are commercially available or methods for their making are known.

Because the magnitude of the diffractive power is dependent on the total spherical power of the lens, computation of the diffractive power for each lens is dependent on the prescription for the individual who use the lens. Thus, the diffractive element is provided on a made-to-order basis. In one method for providing such made-to-order elements, an individual's corrective prescription is determined and a semi-finished blank with the suitable front surface geometry is selected. The front surface of the semi-finished blank may be provided with any suitable coating as, for example, a hard coating, antireflective coating, tinted coating, or the like. Subsequently, the blank is attached to a rotationally symmetrical holding fixture on the front surface so that the fixture is aligned with an optical reference point, such as the optical center. The blocked blank may then be machined on a multi-axis, computer numerically controlled diamond turning machine to form the desired surface, for example sphere, toric, progressive addition, on the back surface that includes the diffractive element. Preferably, machining is carried out by a single point diamond tool mounted on a computer controlled, two axis, linear drive. The surface to be machined may be described by any convenient method including, without limitation, by describing the surface in terms of x, y, and z coordinates or by a set of polynomials each with a set of coefficients and boundary conditions. The machined surface may subsequently be coated with any desired coating.

Although the invention may find particular utility in the design of spectacle lenses, the refractive and diffractive elements may be applied to any type of lens for correction of visual acuity such as a spectacle lens, a contact lens, or an intraocular lens, and the like. The invention will be clarified further by a consideration of the following, non-limiting examples.

EXAMPLES

Example 1

Figure 3:
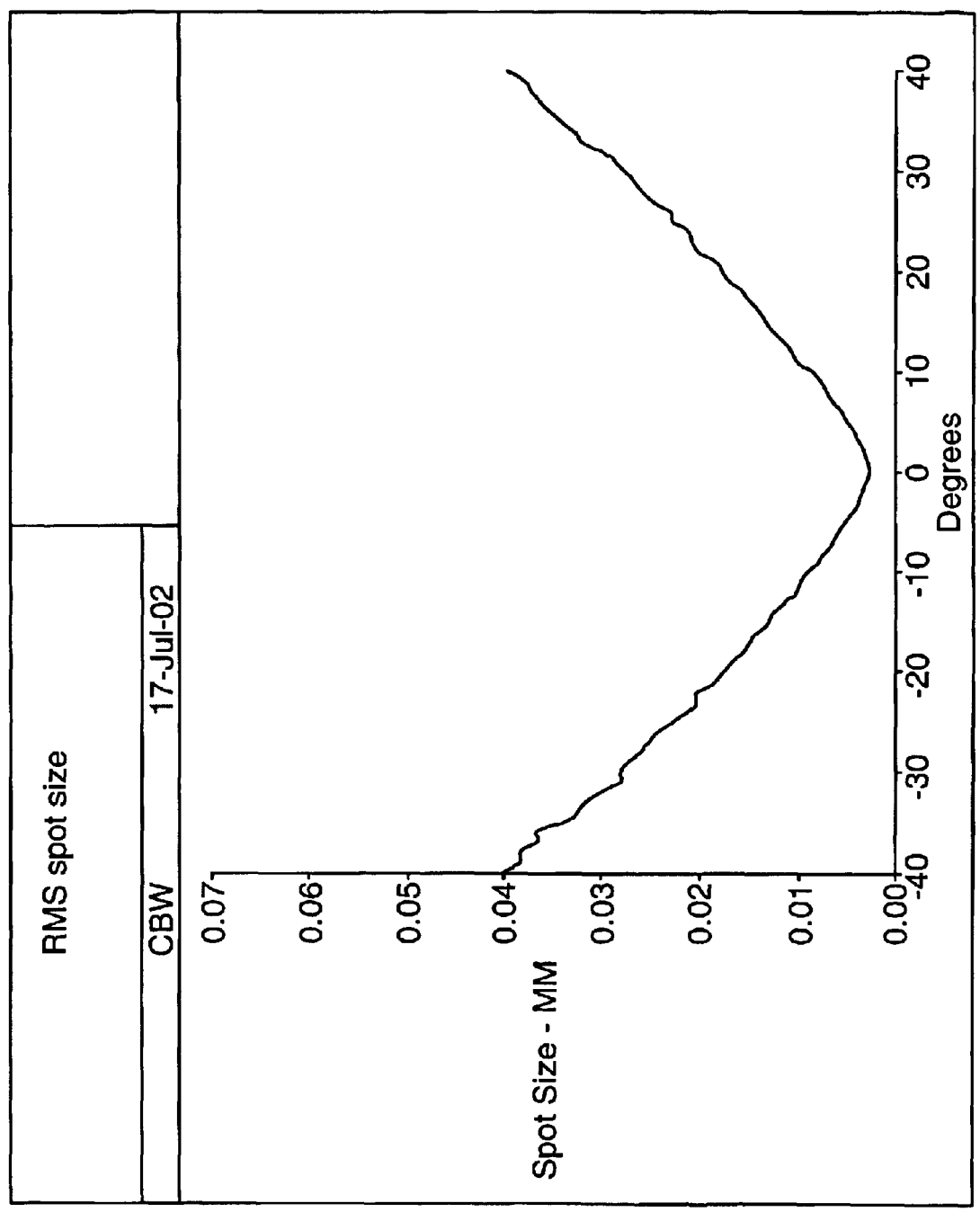
FIG. 3 depicts a cross-section through the lens of the RMS spot size produced by a conventional refractive single vision lens analyzed from the perspective of the eye.

A single vision lens with −4.00 diopters of spherical power is made from polycarbonate with an Abbe number of 29. As a baseline for comparison purposes, a conventional refractive lens is first analyzed, which lens has a front radius of 200 mm and back radius of 79 mm. The lens is analyzed by computing the RMS spot size at the focal plane of an 18 mm focal length lens placed at the eye rotation point 27 mm from the lens. The RMS spot size is computed for input angles from −40 to +40 degrees and is shown in FIG. 3.

A diffractive element with a power of −0.37 diopters is placed on the back, concave, surface of the lens. To maintain the spherical power, the radius of the back surface is changed to 89 mm. The RMS spot size for this diffractive/refractive lens is shown in graphical form in FIG. 4. The image quality at x=0, y=0 improved as measured by the decrease in spot size from approximately 0.004 mm to 0.001 mm. This is due primarily to an improvement in the axial, or longitudinal, aberration. The improvement in image quality is more pronounced for off-axis angles of incidence. For example, at x=0, y=−20 degrees the RMS spot size is 0.017 mm for the conventional refractive lens, but 0.003 mm for the lens with the diffractive element.

Example 2

Figure 4:
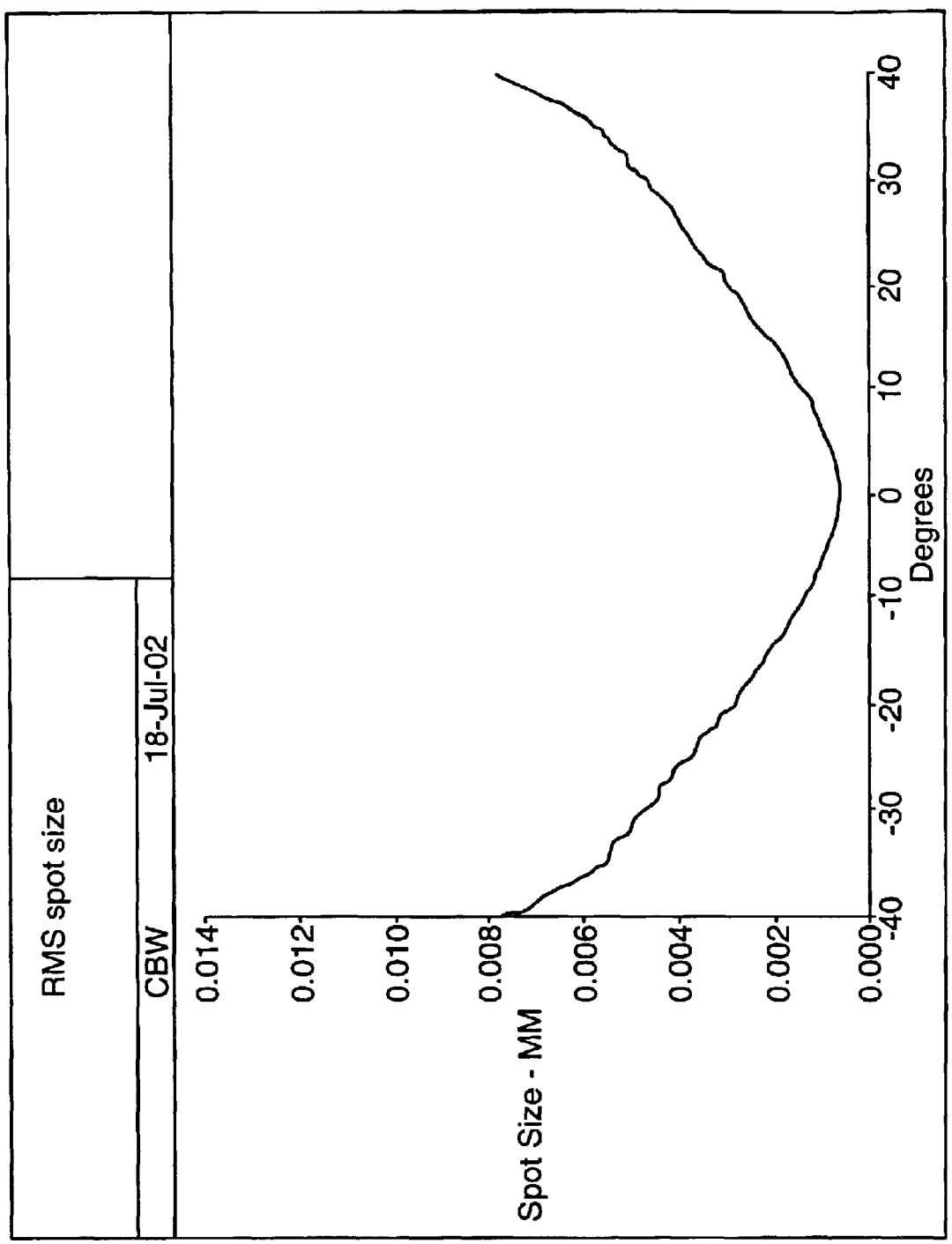
FIG. 4 depicts a cross-section through the lens of the RMS spot size produced by a lens of the invention analyzed from the perspective of the eye.
Figure 5:
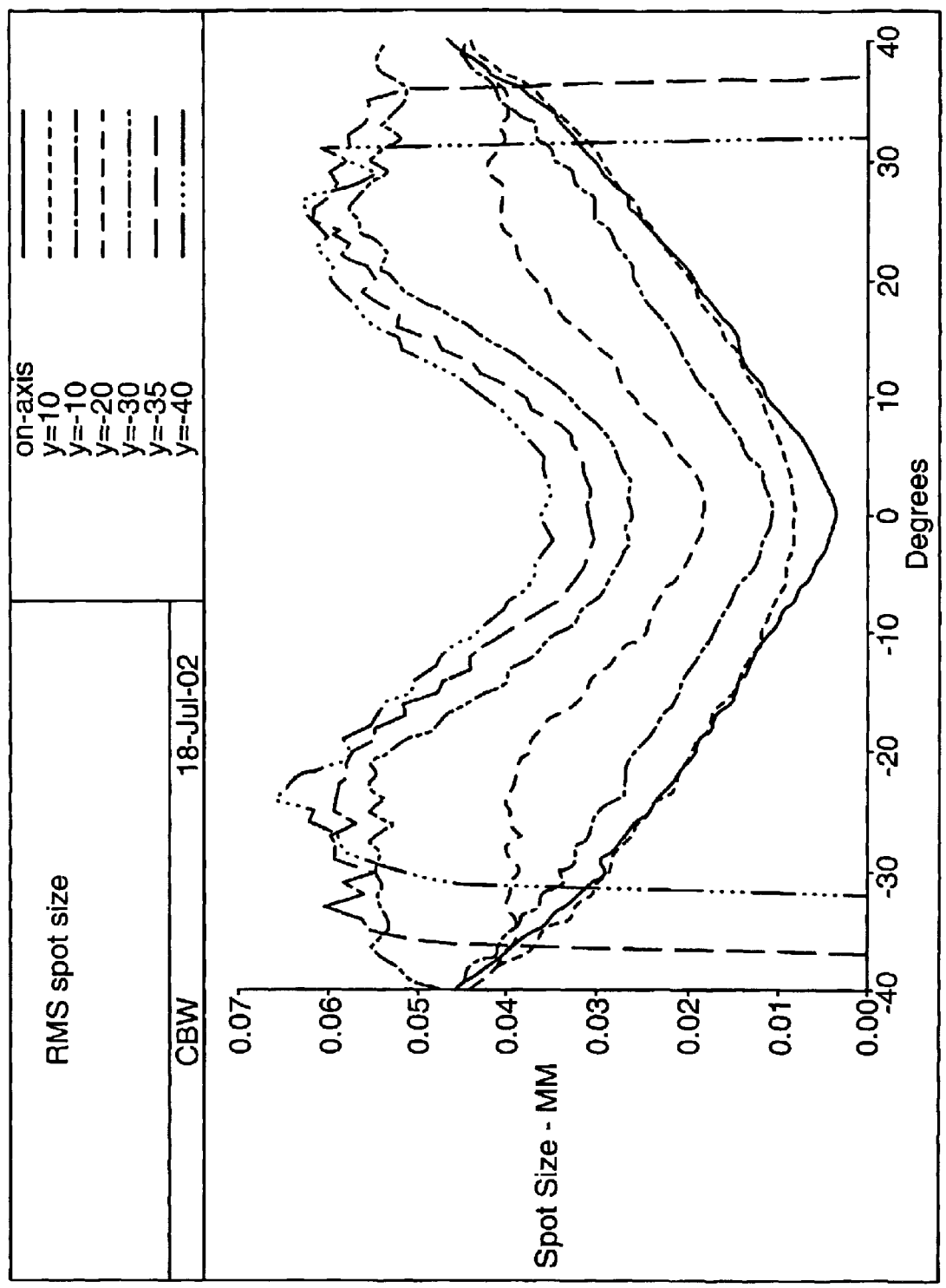
FIG. 5 is a cross-section through a conventional lens at various vertical positions of the RMS spot size.

A polycarbonate, non-toric, progressive addition lens is provided with a distance power of −4.00 diopters and an add power of 1.30 diopters. In FIG. 5 is depicted the RMS spot size for the lens. In FIG. 4 is depicted the unwanted astigmatism in the lens. In both of these figures is shown cross-sectional analysis through horizontal cuts through the lens at various angles. The 10-degree cross-section is a horizontal cut through the far vision region of the lens. In this particular lens, the near vision region is at −40 degrees. A series of cuts is made from the far vision region through the intermediate vision region and to the near vision region.

Figure 6:
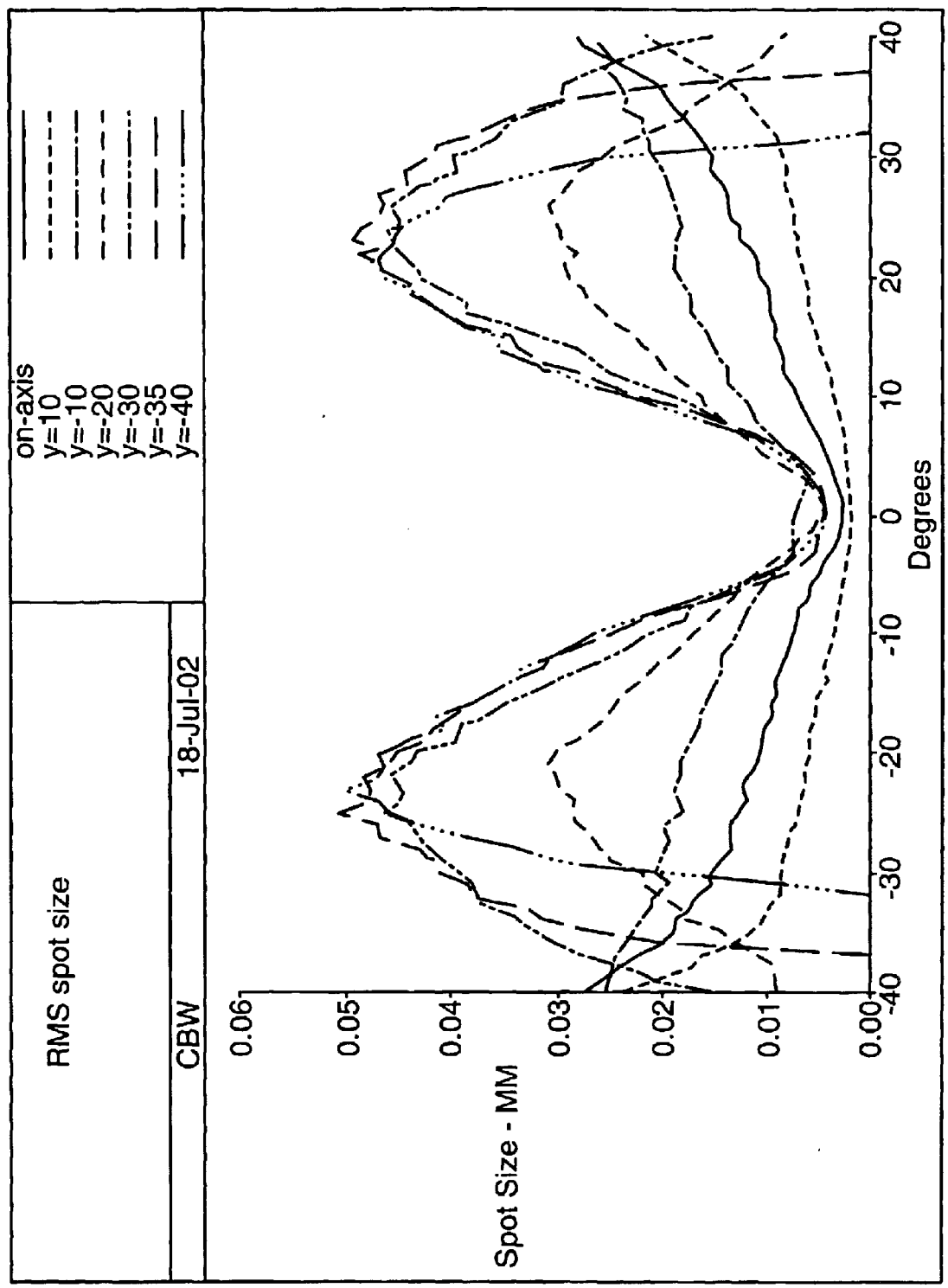
FIG. 6 is a cross-section through a lens of the invention at various vertical positions of the RMS spot size.
Figure 7:
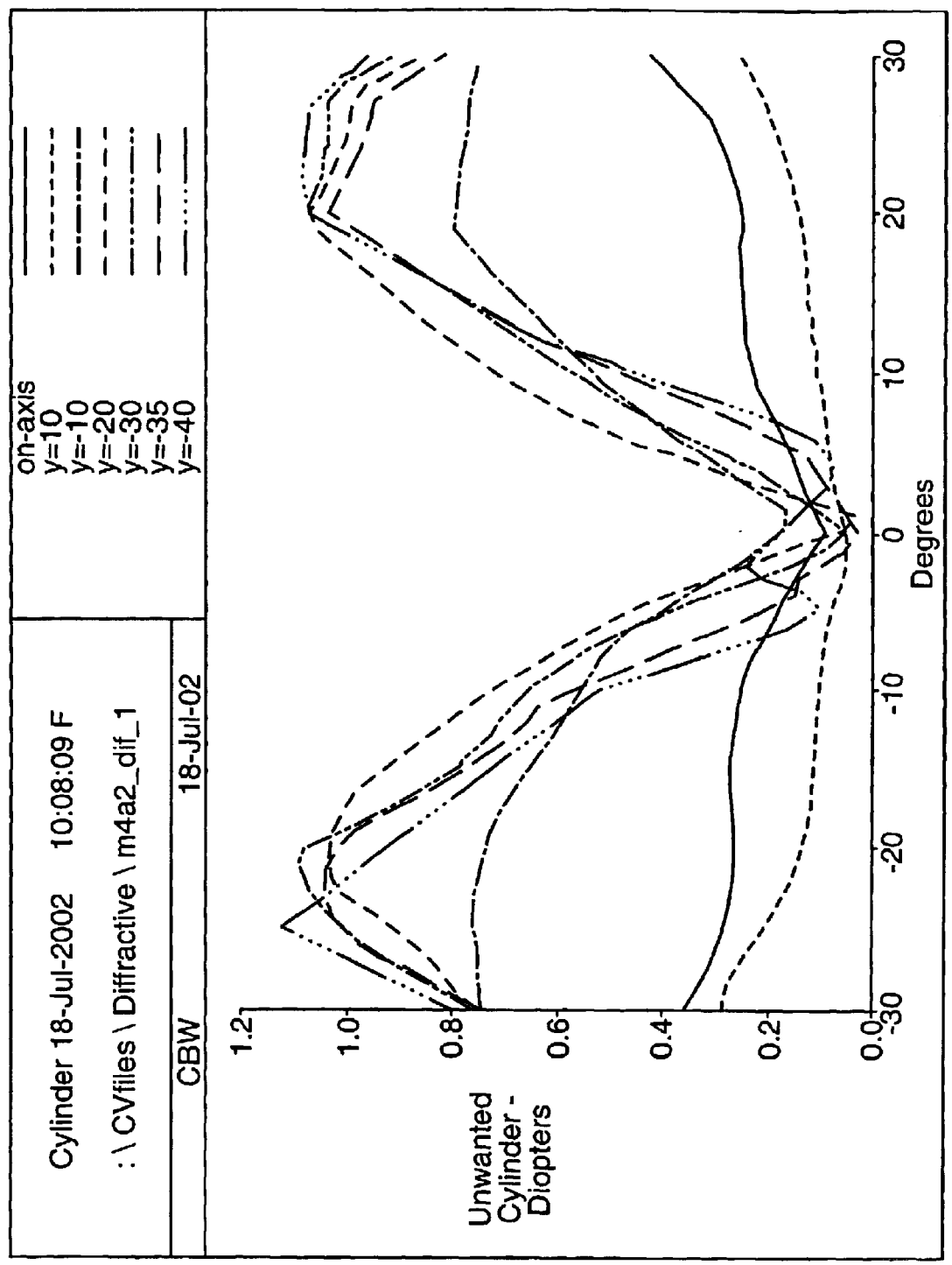
FIG. 7 is a cross-section through a conventional lens at various vertical positions showing unwanted cylinder.
Figure 8:
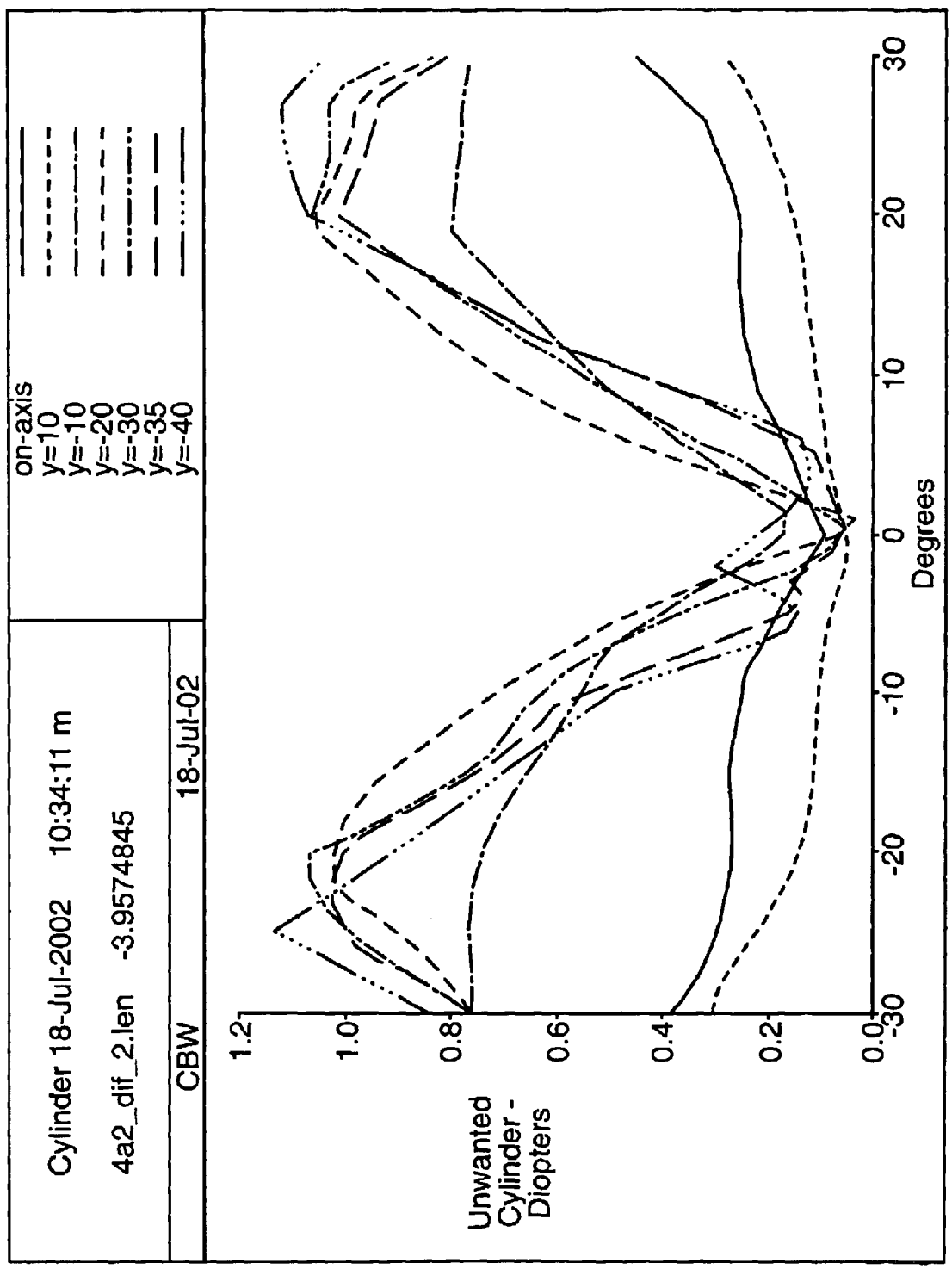
FIG. 8 is a cross-section through a lens of the invention at various horizontal positions showing unwanted cylinder.

A diffractive grating with a −0.35 diopters of power is added on the concave surface of the lens. The overall sphere power remains −4.00 diopters, but the refractive portion of the sphere power was reduced to −3.65 diopters. The Abbe number of the diffractive portion of the lens was approximately −3.5 and that of the refractive portion 29. As shown in FIG. 6, the image quality improved most dramatically along the central meridian, or center of the channel, of the lens. The improvement is obtained without any increase in unwanted astigmatism in the lens as illustrated in FIG. 8.

Example 3

The diffractive power for a family of designs can be chosen so that a unique diffractive is not required for each sphere power. The total spherical power for a lens is the sum of the refractive power of the front surface plus the refractive power of the back surface plus the diffractive power of the diffractive element, whether it is applied to the front, back, or to an intermediate surface.

Table 2 shows the front refractive, back refractive, and diffractive powers for a family of designs for single vision lenses made from polycarbonate that will provide improved chromatic performance because of the diffractive power provided on five of six unique front curves (9, 8, 6, 4, 2, and 1 Diopters). For each sphere power there is a unique back curve. The transverse chromatic aberration at a height of 15 mm on the lens is also shown. The diffractive power was chosen for each of the six unique front curves to give the minimum TCA over the range of sphere powers covered by that case. For the case with a 4 diopter front surface refractive power, the diffractive power chosen was 0 diopters because this still satisfied the constraint given by Equation VII.

TABLE 2

| Total Sphere Power | Front Refractive Power | Diffractive Power | Back Refractive Power | TCA |
|---|---|---|---|---|
| 8 | 9 | 0.80 | −1.80 | 0.026 |
| 7 | 9 | 0.80 | −2.80 | −0.026 |
| 6 | 8 | 0.58 | −2.58 | 0.026 |

TABLE 2-continued

| Total Sphere Power | Front Refractive Power | Diffractive Power | Back Refractive Power | TCA |
|---|---|---|---|---|
| 5 | 8 | 0.58 | −3.58 | −0.026 |
| 4 | 6 | 0.32 | −2.32 | 0.052 |
| 3 | 6 | 0.32 | −3.32 | 0.000 |
| 2 | 6 | 0.32 | −4.32 | −0.052 |
| 1 | 4 | 0.00 | −2.95 | 0.054 |
| 0 | 4 | 0.00 | −3.95 | 0.003 |
| −1 | 4 | 0.00 | −4.95 | −0.049 |
| −2 | 4 | 0.00 | −5.95 | −0.101 |
| −3 | 2 | −0.43 | −4.57 | 0.052 |
| −4 | 2 | −0.43 | −5.57 | 0.000 |
| −5 | 2 | −0.43 | −6.57 | −0.052 |
| −6 | 1 | −0.74 | −6.26 | 0.052 |
| −7 | 1 | −0.74 | −7.26 | 0.000 |
| −8 | 1 | −0.74 | −8.26 | −0.052 |

What is claimed is:

1. An ophthalmic lens, comprising a spherical power $\Phi$, a diffractive element comprising a first spherical power $\Phi_D$ and a refractive element comprising a second spherical power $\Phi_R$, wherein the diffractive element comprises a material having an Abbe number of about 30 to about 60, wherein:

$$\left| \frac{\Phi_R}{V_R} + \frac{\Phi_D}{V_D} \right| = 0$$

and wherein $V_R$ is the Abbe number of the refractive element of the lens and $V_D$ is an effective Abbe number of the diffractive element of the lens.

2. The lens of claim 1, wherein the diffractive element comprises a diffractive power of:

$$2 \left| \frac{\Phi}{1 - \frac{V_R}{V_D}} \right| > |\Phi_D| > 0.$$

3. The lens of claim 1, wherein the diffractive element comprises a diffractive power of:

$$1.5 \left| \frac{\Phi}{1 - \frac{V_R}{V_D}} \right| > |\Phi_D| > .5|\Phi_D|.$$

4. The lens of claim 1, wherein the diffractive element comprises a diffractive power of:

$$\left[ V_D \cdot \frac{\left( \frac{-TCA}{0.1 \cdot y} \cdot V_R - \Phi \right)}{V_R - V_D} \right] > \Phi_D > V_D \cdot \frac{\left( \frac{TCA}{0.1 \cdot y} \cdot V_R - \Phi \right)}{V_R - V_D}.$$

5. The lens of claim 1, 2, 3 or 4, wherein the diffractive element comprises substantially the entire back surface of the lens.

6. The lens of claim 1, 2, 3 or 4, wherein the diffractive element comprises substantially the entire front surface of the lens.

7. The lens of claim 1, 2, 3 or 4, wherein the diffractive element comprises a surface intermediate a front and a back surface of the lens.

8. The lens of claim 5, wherein the lens comprises a single vision lens.

9. The lens of claim 6, wherein the lens comprises a single vision lens.

10. The lens of claim 7, wherein the lens comprises a single vision lens.

11. The lens of claim 5, wherein the lens comprises a multifocal lens.

12. The lens of claim 6, wherein the lens comprises a multifocal lens.

13. The lens of claim 7, wherein the lens comprises a multifocal lens.

14. A method for producing a customized lens comprising the step of providing a lens comprising a spherical power $\Phi$, a diffractive element comprising a first spherical power $\Phi_D$ and a refractive element comprising a second spherical power $\Phi_R$, wherein the diffractive element comprises a material having an Abbe number of about 30 to about 60, wherein:

$$\left| \frac{\Phi_R}{V_R} + \frac{\Phi_D}{V_D} \right| = 0$$

and wherein $V_R$ is the Abbe number of the refractive element of the lens and $V_D$ is an effective Abbe number of the diffractive element of the lens.

15. The method of claim 14, wherein the lens is a single vision lens.

16. The method of claim 14, wherein the lens is a multifocal lens.

* * * * *